(12) United States Patent
Kay et al.

(10) Patent No.: US 6,411,850 B1
(45) Date of Patent: Jun. 25, 2002

(54) METHOD OF DETERMINING A VENTILATORY THRESHOLD BREAKPOINT FOR AN ADAPTIVE RATE PACEMAKER

(75) Inventors: G. Neal Kay, Birmingham, AL (US); Donald L. Hopper, Maple Grove, MN (US); Jan-Pieter Heemells, Zaventem (BE); Jeff Hall, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/408,623

(22) Filed: Sep. 30, 1999

(51) Int. Cl.$^7$ ................................................. A61N 1/36
(52) U.S. Cl. ........................................... 607/20; 607/19
(58) Field of Search ................................ 607/17–20, 9; 600/534–536, 547

(56) References Cited

U.S. PATENT DOCUMENTS

| | | | |
|---|---|---|---|
| 4,901,725 A | 2/1990 | Nappholz et al. | 128/419 |
| 5,201,808 A | 4/1993 | Steinhaus et al. | 128/419 |
| 5,303,702 A | 4/1994 | Bonnet et al. | 607/20 |
| 5,487,753 A | 1/1996 | MacCarter et al. | 607/17 |
| 5,578,064 A | 11/1996 | Prutchi | 607/19 |
| 5,800,469 A | 9/1998 | Nappholz | 607/18 |
| 5,931,858 A | * | 8/1999 | Kadhiresan et al. | 607/20 |

FOREIGN PATENT DOCUMENTS

| | | | |
|---|---|---|---|
| EP | 0 804 938 A2 | 11/1997 | A61N/1/365 |

OTHER PUBLICATIONS

Lewalter et al., The "Low Intensity Treadmill Exercise" Protocol for Appropriate Rate Adaptive Programming of Minute Ventilation Controlled Pacemakers, PACE, 18:1374–1387 (Jul. 1995).

International Search Report dated Jan. 2, 2001; International Application No. PCT/US00/26283.

* cited by examiner

Primary Examiner—Kennedy Schaetzle
Assistant Examiner—Kristen Doresch
(74) Attorney, Agent, or Firm—Myers Bigel Sibley & Sajovec (57) ABSTRACT

A method for automatically determining the ventilatory (or "anaerobic") threshold breakpoint for adaptive rate pacing without the need for directly measuring anaerobic threshold or ventilatory threshold comprises: (a) positioning a first sensing electrode in the heart or superior vena cava of a patient carrying an implanted pacemaker, the first sensing electrode connected to the implanted pacemaker; (b) positioning a second sensing electrode in the thoracic region of the patient and spaced apart from the first sensing electrode; (c) determining the chest wall impedance of the patient between the first sensing electrode and the second sensing electrode; (d) measuring the ventilation (e.g., the minute ventilation) of the subject from the chest wall impedance during submaximal exercise by the patient; and then (e) determining the ventilatory threshold breakpoint of the patient from the measured ventilation. In the pacemaker, the adaptive rate pacing is preferably based on measured chest wall impedance, with pacing rate increasing as exercise or metabolic activity sensed thereby increases. The implanted pacemaker is then preferably programmed, preferably automatically, so that the rate of increase in pacing rate in response to increasing ventilation by the pacemaker is attenuated after the breakpoint is reached. Peak ventilation is preferably also determined so that the maximum pacing rate of the pacemaker output is matched to the peak ventilation during adaptive rate pacing from the pacemaker. Apparatus implementing the method is also disclosed.

21 Claims, 6 Drawing Sheets

METHOD OF DETERMINING A VENTILATORY THRESHOLD BREAKPOINT FOR AN ADAPTIVE RATE PACEMAKER

FIELD OF THE INVENTION

The present invention concerns an adaptable rate pacemaker method and apparatus in which the ventilatory (or anaerobic) threshold break point is determined without the need for a maximal exercise test.

BACKGROUND OF THE INVENTION

Implanted cardiac pacemakers are employed to assist patients suffering from electrical conduction disorders of the heart. Such pacemakers originally restored a normal heart rate by providing a single fixed rate of paces, or a narrow range of externally programmable pacing rates. These early pacemakers failed to meet patients' metabolic demands during exercise. Consequently, so-called "rate adaptive" or "rate responsive" pacemakers have been developed. These pacemakers sense any of a variety of different parameters that are correlated to physiologic need and adjust the pacing rate of the pacemaker in response thereto. See generally U.S. Pat. No. 5,578,064 to Prutchi. Rate adaptive pacemakers require (a) an input parameter which can be monitored as an indication of the metabolic need of the patient, and (b) a program or model by which the pacing rate delivered to the patient by the pacemaker at a particular time is determined from the input parameter.

In normal subjects, pulse is commonly monitored as an indication of a subject's metabolic need during work or exercise. Of course, in patients requiring a pacemaker, a pulse is not available as an input parameter because the pulse is driven by the pacing rate of the pacemaker itself. Accordingly, common input parameters for adaptive rate pacemakers are stroke volume of the heart and the minute volume of respiration, both of which can be inferred from impedance measurements. See, e.g., U.S. Pat. No. 5,578,064 to Prutchi, U.S. Pat. No. 5,201,808 to Steinhaus et al.; and U.S. Pat. No. 4,901,725 to Nappholz et al. The problem of establishing a model to determine the pacing rate to be given in response to a particular input parameter is a separate issue.

T. Lewalter et al., PACE 18, 1374 (1995), describes a low intensity treadmill exercise (LITE) protocol for rate adaptive programming of minute ventilation controlled pacemakers. The purpose of the study was to determine the physiological relationship between heart rate and minute ventilation (HR/VE) during peak exercise testing, to develop a database for appropriate rate adaptive slope programming of minute ventilation controlled pacemakers. As an alternative to peak exercise testing, the LITE protocol was used. The LITE protocol was performed on a treadmill with the collection of breath-by-breath gas exchange, and linear regression analysis used to determine the HR/VE slope below and above the anaerobic threshold and during the early, dynamic phase of low intensity exercise with the LITE and the ramped incremental treadmill exercise (RITE). It was determined that the LITE protocol can be performed as a substitute for peak exercise stress tests to determine the correct pacemaker rate response factor in order to obtain a physiological heart rate to minute ventilation relationship for the appropriate matching of paced heart rate with patient effort. A problem with this procedure is, however, the need for extrinsic minute volume measurement with an external flow sensor. This requires that the procedure be performed in a clinical setting with a treadmill or the like. Thus, the patient is unable to choose the particular exercise on which programming of the pacemaker will be based. It would be preferable to provide a procedure for accurately determining the ventilatory threshold breakpoint for adaptive rate pacing that can be entirely incorporated into an implantable patient device. In this manner, the patient would be able to choose an exercise of any modality, and perform submaximal exercise, and then the device would automatically determine the appropriate adaptive rate pacing response factor.

SUMMARY OF THE INVENTION

A method for automatically determining the ventilatory (or anaerobic) threshold breakpoint for adaptive rate pacing without the need for directly measuring anaerobic threshold or ventilatory threshold in a human subject carrying an implanted pacemaker, is disclosed. The method comprises: (a) positioning a first sensing electrode in the heart or superior vena cava of the patient, the first sensing electrode connected to the implanted pacemaker; (b) positioning a second sensing electrode in the thoracic region of the patient and spaced apart from the first sensing electrode; (c) determining the chest wall impedance of the patient between the first sensing electrode and the second sensing electrode; then (d) measuring the ventilation (e.g., the minute ventilation) of the subject from the chest wall impedance during submaximal exercise by the patient; and then (e) determining the ventilatory threshold breakpoint of the patient from the measured ventilation.

The second sensing electrode is typically positioned outside the pleural cavity of the patient, and is preferably positioned on the surface of the implanted pacemaker. A preferred embodiment of the invention further includes the step of measuring respiratory rate (RR) concurrently with the step of measuring the ventilation of the subject. The determining step then comprises determining the ventilatory threshold breakpoint of the patient from both the measured ventilation during submaximal exercise and the measured respiratory rate during submaximal exercise. Preferably the method is implemented by calculating a parameter (e.g., by regression analysis) from the measured ventilation, with the parameter being respiratory rate change during submaximal exercise, tidal volume change during submaximal exercise, or tidal volume during steady state submaximal exercise, and then determining the ventilatory threshold breakpoint from at least one of those calculated parameters. Peak ventilation can be determined in like manner.

One preferred embodiment of the foregoing method further includes the steps of: (i) determining the onset slope of tidal volume ($V_t$) during the submaximal exercise; (ii) determining the onset slope of respiratory rate (RR) during the submaximal exercise; (iii) determining the steady state of $V_t$ during the submaximal exercise; (iv) determining the steady state of RR during the submaximal exercise; and (v) determining minute ventilation (VE) during a rest period prior to or following the submaximal exercise. The determining step then comprises determining the ventilatory threshold breakpoint of the patient from all of the measured ventilation during submaximal exercise; the measured respiratory rate; the onset slope of tidal volume during the submaximal exercise; the onset slope of respiratory rate, the steady state of $V_t$ during submaximal exercise; and the steady state of RR during the submaximal exercise; VE during the submaximal exercise; and VE during the rest period.

The measuring step may be initiated under operator control, which operator may be the patient, a medical professional, or other. Once the ventilatory threshold breakpoint is determined, the pacemaker may then be programmed to reduce the rate of increase in the pacing rate (which is typically increased in rate in response to detection of increased ventilation by the chest wall impedance sensor) at the determined ventilatory threshold breakpoint. The programming step is preferably carried out automatically, without further operator intervention. Further, the pacemaker is preferably programmed so that the maximum pacing rate is matched to and delivered upon attaining the peak ventilation, which peak ventilation is determined as described above.

A second aspect of the present invention is a rate-responsive cardiac pacemaker. The pacemaker comprises a pacing circuit configured for pacing a patient's heart as a function of a pacing signal at a pacing rate up to a maximum pacing rate; a sensing circuit configured to sense ventilation by said patient; and a control circuit operatively associated with said sensing circuit and configured (via hardware, software, or combinations thereof, implementing the methods described above) to determine a ventilatory threshold break point from the sensed ventilation. In use, the pacing signal is modified by sensed ventilation (and optionally other signals). The control circuit is configured to modify the pacing rate in response to the ventilatory threshold break point determined thereby. In addition, the control circuit is preferably configured to determine a peak ventilation in response to the sensed ventilation, and match that sensed ventilation to the maximum pacing rate of the device (i.e., so that the maximum pacing rate is delivered when the peak ventilation is detected).

BRIEF DESCRIPTION OF THE DRAWINGS

FIG. 4 is a metabolic analyzer measurement from a patient, obtained with a MEDGRAPHICS™ oxygen uptake analyzer (Medgraphics Inc., St. Paul, Minn., USA), illustrating an exercise protocol for a patient, from the start of exercise to peak exercise. Increasing workload stages are illustrated by the increasing lines on the graph. The line plotted with the heart symbol indicates respiratory rate in beats per minute (values given on left vertical axis; left side); the line plotted with the diamond symbol indicates the minute ventilation (VE) in Liters per minute (values given on left vertical axis, right side); the line plotted with the spade symbol indicates $VO_2/kg$; in ml/kg/min (values given on right vertical axis; left side); the line plotted in squares indicates subject work in watts (values given on right vertical axis; right side).

DETAILED DESCRIPTION OF THE PREFERRED EMBODIMENTS

Terms and phrases used herein have, in general, their usual meaning in the art, as further explained below.

"Respiratory rate" or "RR" means the number of breaths by a subject over a particular period of time, usually expressed as breaths per minute.

"Tidal volume or "$V_t$" means the volume of air entering or leaving the lungs of a subject during a single breath. Tidal volume may vary depending upon the metabolic demands or degree of exertion of the subject.

"Ventilation" means the total pulmonary ventilation during a particular period of time, and is usually determined by the tidal volume times the respiratory rate. When the respiratory rate is expressed as breaths per minute, the "ventilation" is the "minute ventilation" or "VE".

"Onset slope of respiratory rate" means the slope of the change in respiratory, rate over time from the respiratory rate at rest to the respiratory rate at a new level of exercise (e.g., submaximal exercise).

"Steady state of respiratory rate", such as during submaximal exercise, means a substantially constant respiratory rate during a substantially constant workload for a certain exercise over a given period of time (e.g., a period of three minutes).

"Peak ventilation" means the minute ventilation at maximal exercise.

"Onset slope of tidal volume" means means the slope of the change in tidal volume over time from the tidal volume at rest to the tidal volume at a new level of activity (e.g., submaximal exercise).

"Steady state of tidal volume", such as during submaximal exercise, means a substantially constant tidal volume during a substantially constant workload for a certain exercise over a given period of time (e.g., a period of three minutes).

"Ventilatory threshold breakpoint" means a point during exercise when ventilation increases logarithmically as compared to heart rate due to increased metabolic demand.

"Rest" or "rest period" means a time of quiet, seated activity for an awake subject, where no other work is required, after sufficient time to reach a stable base line of respiration (typically 10–15 breaths per minute).

"Exercise" refers to any activity by a subject that requires more exercition than rest, including but not limited to walking, running, swimming, cycling, gardening, household chores, etc.

"Submaximal exercise" means any exercise carried out at a level of effort, or workload, less than maximum.

"Maximal exercise" means any exercise carried out at a maximum level of effort or maximum workload; a point during exercise when the subject has reached the maximum amount of oxygen they can consume and are incapable of increasing their workload.

"Subject" or "patient" as used herein refers to a human subject or patient, which may be a male or female of any age, typically an adult. Subjects of the present invention are typically afflicted with an electrical conduction disorder of the heart which may be treated by the implantation and use of a cardiac pacemaker. Such disorders include, but are not limited to, bradycardia, chronotropic incompetence, impaired A-V nodal conduction, chronic refractory tachyarrhythmia, atrial tachyarrhythmia, low cardiac output, etc.

The present invention uses impedance measured minute ventilation to determine the peak ventilatory threshold. Prior pacemakers incorporated programmable parameters that estimated the ventilatory threshhold and no method of determining the peak ventilatory threshold without a peak exercise evaluation. The method of the invention is carried out to automatically determine the ventilatory threshold break point, at which the relationship of pacing rate or heart rate delivered by the adaptive rate pacemaker should be attenuated. In addition, the methods of the invention provide the ability to determine the peak ventilation that should occur at the maximal heart rate or pacing rate performed. These two features eliminate the need for specific program features of lifestyle or age to determine the ventilatory or anaerobic threshold break point, and automatically determines the aggressiveness of the rate response slope by determining and matching the maximal pacing rate to the peak ventilation. This provides an "automatic" minute ventilation sensor, allowing the physician to implant the pacemaker with no need to adjust the rate responsive algorithm.

Figure 1:
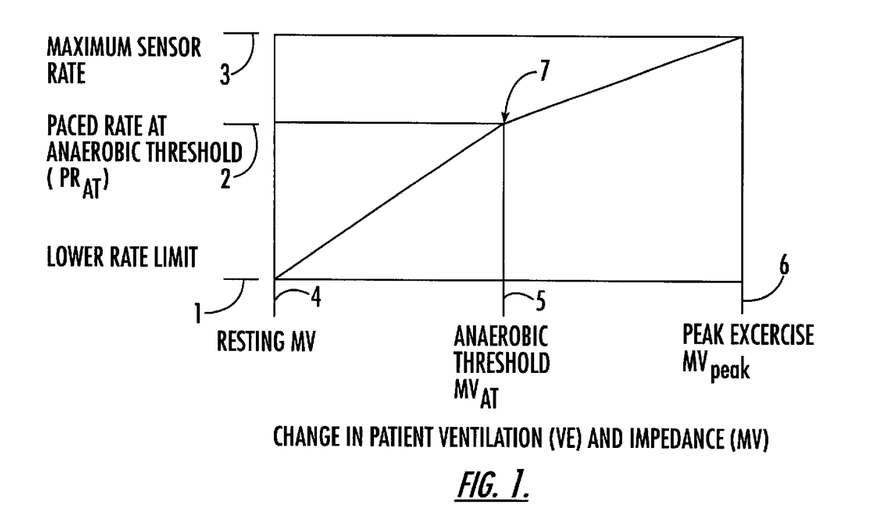
FIG. 1 is a graph showing the relationship of patient pacing rate on the vertical axis to changes in the patient minute volume on the horizontal axis.

The present invention provides a regression model by which parameters useful for the operation of a minute volume sensor are automatically determined. FIG. 1 shows the parameters that are employed to set up an apparatus of the invention. In FIG. 1, pacing rate is given on the vertical axis, and minute volume is given on the horizontal axis. Pacing rate progresses from the lower rate limit 1, to the paced rate at the anaerobic threshold ($PR_{AT}$) 2, to the maximum pacing rate 3. Minute volume (MV) progresses from the resting MV 4, to the anaerobic threshold MV ($MV_{AT}$) 5, to the peak exercise MV ($MV_{peak}$) 6. The break point 7 represents the point at which the rate of increase in pacing rate is attenuated for further increases in minute volume.

Figure 2:
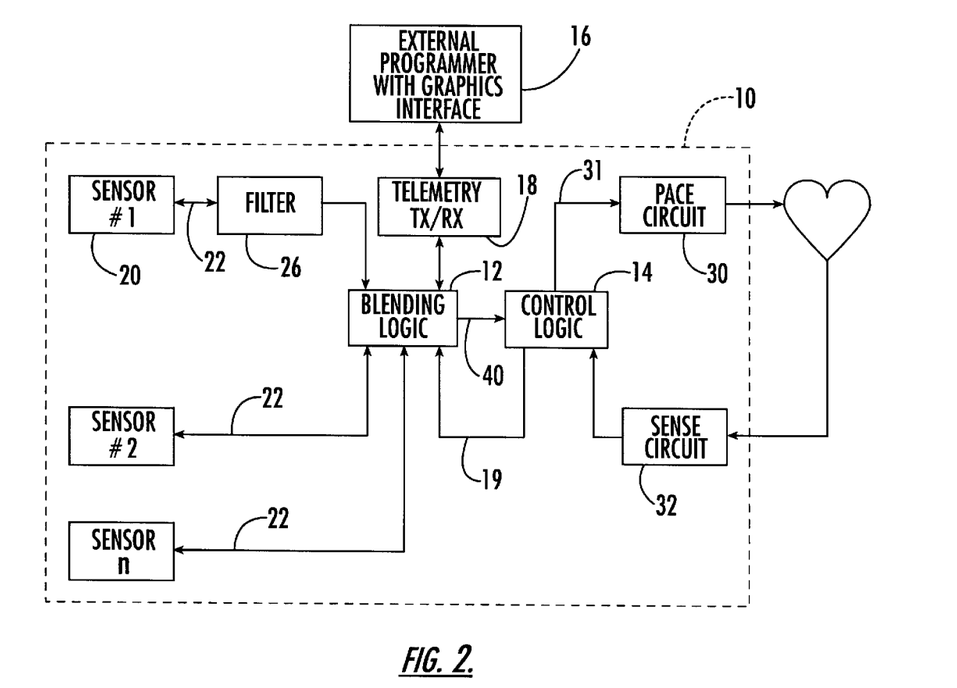
FIG. 2 is a block diagram of a rate responsive pacemaker that can be used to carry out the present invention.

The method of the present invention can be implemented in any suitable rate adaptive pacemaker, including but not limited to that described in U.S. Pat. No. 5,376,106 to Stahmann et al. (the disclosures of all patent references cited herein are to be incorporated by reference herein in their entirety). In general, and as illustrated in FIG. 2, such a pacemaker 10 includes a blending logic circuit 12 which arbitrates and/or combines delta pacing rate signals from two or more sensors, which sensors provide physical and physiological parameters of the patient. Blending logic circuit 12 mixes or blends the delta pacing rate signals from each of the sensors based on a predetermined, but preferably variable ratio. This ratio defines the percentage or portion of each of the sensor signals which comprise a single delta pacing rate signal provided by the blending logic circuit 12 to control logic circuit 14 via line 40. Control logic 14 determines a pacing rate as a function of the single delta pacing rate signal and instructs pacing circuitry 30 via line 31 to pace the heart at the pacing rate.

A plurality of sensors 20, comprised of any well known physical and physiological sensors typically implemented in rate responsive pacemakers, form a portion of pacemaker circuit 10. For instance, accelerometers for measuring physical movement, impedance sensors employed to sense minute ventilation, temperature sensors, blood pressure sensors, and pH sensors all can be employed in the present invention. Each of these sensors include some form of signal processing, such as sample averaging, such that upon sensing the respective physical or physiological parameter, the signal output from the respective sensor is indicative of a delta pacing rate. The signals outputted from each of sensors 20 are provided on respective output lines 22, and are provided in either a digital or analog format. In the preferred embodiment, all signal processing is done digitally, however, limitation to a digital implementation is not to be inferred. As will be apparent, the present invention is preferably carried out with at least a chest wall impedance minute volume sensor for determining the pacing rate, with other sensors optionally included as well.

Pacemaker circuitry 10 also includes a filter 26 inserted between sensor number 1 and the blending logic circuit 12 to alternate suspect signals, such as prolonged signals from an accelerometer as the patient traverses over a rough road in a car, before the outputted signal is applied to the equations in blending logic circuit 12. While filter 26 is shown interposed between one sensor 20 and blending logic 12, it is recognized in the art that an appropriate filter 26 could be implemented for one or more sensor, and defined integral to the respective sensor 20 itself, or implemented in. the blending. logic circuit 12, and limitation to a discrete filter interposed therebetween is not to be inferred. For instance, when processing the sensor signals in the digital implementation, filter 26 will unilaterally condition the respective signal before it is communicated to blending logic circuit 12 and there applied to the equations. If, for instance, analog signal processing techniques are implemented, a high pass filter can be used to reduce the signal level before it is communicated to blending logic circuit 12. Thus, when one of the sensor inputs is accelerometer based and the other is not, such as minute ventilation, temperature, cardiac impedance, etc., the present invention provides a method for limiting consideration of the rate increase from sensor number one due to misleading physical motion over time.

Control logic 14, blending logic 12, pace circuit 30, and sensing circuit 32 are known in the art. Blending logic 12 is not essential in carrying out the present invention. The invention can be carried out or implemented in a variety of pacemaker configurations or with a variety of combination of features, including but not limited to those described in U.S. Pat. No. 5,376,106 to Stahmann et al.; U.S. Pat. No. 5,318,597 to Hauck et al.; U.S. Pat. No. 5,423,870 to Olive et al.; U.S. Pat. No. 5,755,740 to Nappholz, U.S. Pat. No. 5,814,087 to Renirie; and U.S. Pat. No. 5,562,711 to Yerich et al, the disclosures of all of which applicants specifically intend to be incorporated herein by reference.

The control logic 14 is configured or programmed to implement the breakpoint as illustrated in FIG. 1 for the particular subject in which the pacemaker 10 is implanted. Since it is preferred to avoid measuring the $PR_{AT}$, $MV_{AT}$ and $MV_{peak}$ in each and every patient, the present invention provides a way to predict these values from readily available information. The technique disclosed herein can accurately estimate the values for these parameters using parameters such as tidal volume change during submaximal exercise, respiratory rate change during submaximal exercise, tidal volume during steady state submaximal exercise, or combinations thereof. In a particular embodiment, the parameters used are: tidal volume at rest (Vt), respiratory rate (RR), tidal volume steady state exercise (Vtss), respiratory rate steady state (RRss) and the onset slope of Vt, and the respiratory rate from rest to steady state exercise.

In one preferred embodiment of the invention, the present invention is implemented in a PULSAR MAX™ implantable cardiac pacemaker (manufactured by the Guidant Corp. Cardiac Rhythm Management Group, 4100 Hamline Avenue North, St. Paul, Minn. USA 55112–57980), to provide a tool to automatically determine the ventilatory threshold and peak ventilation without performing a maximal exercise test and eliminating programmable parameters, by automatically. matching peak ventilation to maximal pacing rate appropriately.

The anaerobic threshold or ventilatory threshold can be estimated from the above information, as can the peak ventilation seen during maximal exercise (multiple R values of 0.928 and 0.938). The patient can simply perform a submaximal exercise, of any modality, and the pacemaker algorithm measures the onset slope of tidal volume (Vt), onset slope of respiratory rate (RR), steady state of Vt, RR, a resting VE. At this point the control logic will map the rate response to the estimated ventilatory threshold and match maximal pacing rate to estimated peak ventilation. This can be done "on the fly", or during normal patient behavior with data collected over a period of time, the control logic of the device automatically implementing the procedure when sufficient patient data is collected.

Figure 3:
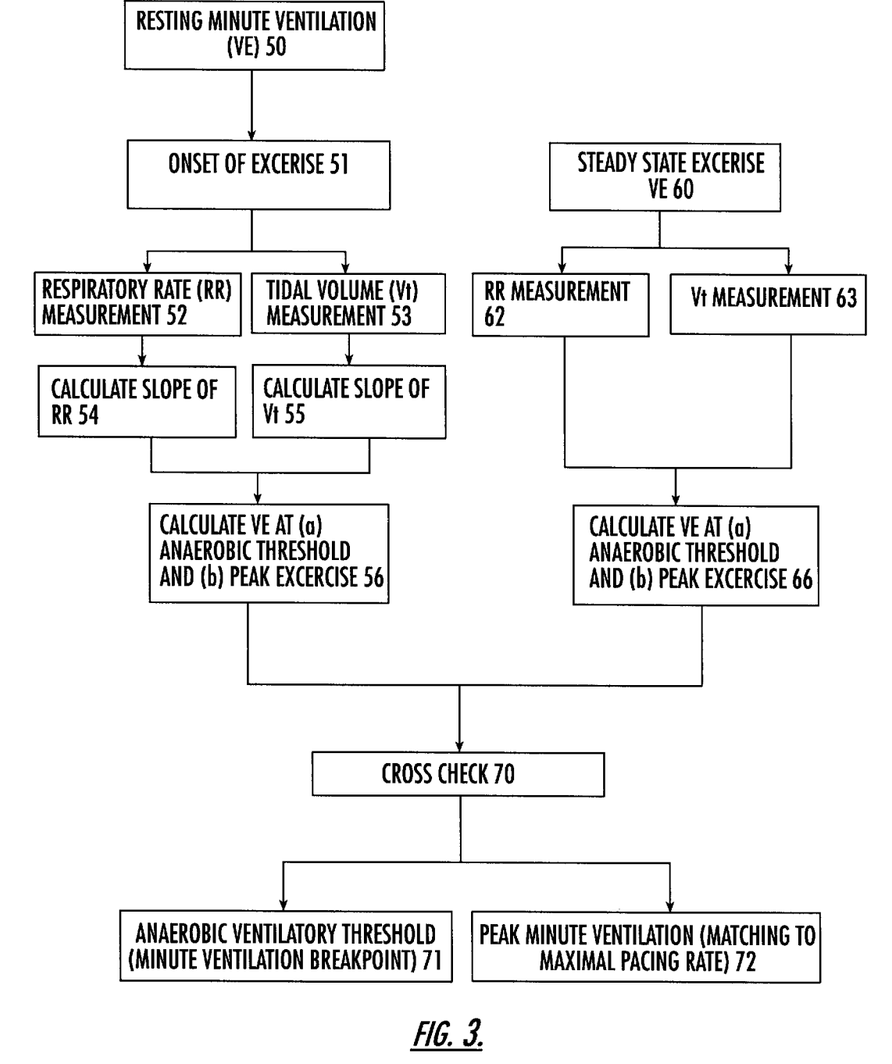
FIG. 3 is a flow chart illustrating the determination of the anaerobic threshold and the peak minute ventilation by a method of the present invention, which can be implemented in an apparatus as shown in FIG. 2.

The estimated parameters needed are determined from the known minute ventilation ratios as diagrammed in FIG. 3. As illustrated on the left-hand side of FIG. 3, a resting minute ventilation 50 is determined. After the onset of exercise 51, respiratory rate (RR) is measured 52 and tidal volume (Vt) is determined 53. The slope or change in respiratory rate during the exercise (which is typically not steady state exercise, but increasing or decreasing exercise, preferably increasing exercise or workload) is then determined 54, along with the slope or change in tidal volume during the exercise 55. The minute ventilation (VE) is then calculated at both the anaerobic threshhold and peak exercise 56.

An alternate way to carry out the invention is illustrated on the right side of FIG. 3. This embodiment is carried out during steady state exercise, during which minute ventilation (VE) is measured 60. The respiratory rate is measured 62 and the tidal volume determined 63. The minute ventilation (VE) is then calculated at both the anaerobic threshhold and peak exercise 66.

As illustrated in FIG. 3, a single apparatus can incorporate both methods, after which the results of both methods are compared or cross-checked 70 with one another. If the results are sufficiently consistent then a ventilatory threshold breakpoint can be given 72 and the peak minute ventilation 72 given. If sufficient inconsistency is noted upon the cross-check, then either result can be rejected, or both can be rejected and the procedure repeated. Whether or not a cross-check is employed, the implantable pacemaker can then be automatically programmed with control logic so that the pacing rate is reduced upon reaching the ventilatory threshold breakpoint, and the maximum pacing rate is matched to the peak minute ventilation.

The data set forth in Table 1 below were collected from a patient in the manner described in connection with FIG. 3 above and analyzed by regression analysis, comparing the respiratory parameters of tidal volume ($V_t$), respiratory rate (RR), minute ventilation (VE), the slope or changing relationships of the respiratory parameters to the onset of exercise, resting state, steady state of exercise and maximal exertional exercise. From this data the following coefficients and constants can build the predictive equations in accordance with standard techniques to estimate the ventilatory threshold and peak ventilation for mapping pacing rate to ventilation changes.

TABLE 1

| Ventilatory Parameter | Anaerobic/ Ventilatory Threshold B Coefficient | Peak Ventilation B Coefficient |
|---|---|---|
| Multiple R | 0.9276 | 0.9382 |
| Constant | −227.789 | −291.789 |
| Vt to Ve slope onset of exercise | −0.6113 | −0.8192 |
| RR to VE slope onset of exercise | −45.724 | −59.741 |
| Vt steady state exercise | 0.370 | 0.437 |
| RR steady state exercise | 12.575 | 15.324 |
| VE steady state | −14.934 | −17.064 |
| Resting VE | −0.791 | 1.1678 |

The present invention is preferably implemented with the PULSAR-MAX™ pacemaker described above, which uses transthoracic impedance to indirectly measure minute ventilation (respiratory rate and tidal volume). Based on the minute ventilation measure, the pacemaker calculates the sensor rate. The base line or resting minute ventilation is used to obtain a relative minute ventilation (two-hour) average measurement which is compared to a short-term (approximately 30-second) average to determine the change in minute ventilation above rest. This increase in minute ventilation above rest is used to increase the sensor rate in correspondence to metabolic demand.

In the PULSAR-MAX™ pacemaker, an increase in minute ventilation over baseline due to an increase in metabolic demand will be detected by the pacemaker and converted by its algorithm into an increased pacing rate. The relationship between the detected. increase in minute ventilation and the resulting increase in rate is established by the minute ventilation Response Factor. The Response Factor parameter determines the pacing rate that will occur above the programmed minimum pacing rate (lower rate limit) at various elevated levels of minute ventilation. Larger Response Factor values will result in higher sensor rates for a given minute ventilation level.

The Automatic Response Factor feature in the PULSAR-MAX™ pacemaker allows the Response Factor to adapt to changes in the sensor-rate relationship over time. When this feature is used, the pacemaker will record the maximum daily sensor rate excursions. Each week, the average of the daily maxima will be compared to the programmed sensor rate target (the sensor rate target is a selected rate that is programmed into the pacemaker by the physician). Whenever the weekly average is more than 5 pulses per minute above or below the selected sensor rate target, the Response Factor will be increased or decreased respectively.

Thus, previous implimentations of minute ventilation devices have relied upon maunal programming of the Response Factor or the adaptiation of the Response Factor to a selected pacing rate over time. There has not been an attempt to have a pacemaker automatically determine the appropriate Response Factor slope to provide appropriate mapping of a patient's ventilatory reserve to their heart rate reserve via artificially pacing the heart. A pacemaker of the present invention, which automatically determins a patient's minute ventilation at the anaerobic threshold and peak exercise via a physiological change in their ventilatory properties, reduces the programming effort of physicans and the guess work of programming adaptive rate pacemakers. In use, the physician would simply implant the device and the device would start collecting minute ventilation data from the patient via impedance measurements. The device would collect a resting baseline measurement as described in the prior PULSAR-MAX™ pacemaker. Control logic in the device would then determine the change in minute ventilation from rest to a resulting steady state work or exercise that the patient has performed, as described in connection with FIG. 3 above. Once the device has a reliable measurement of this increase in metabolic work (rest to some submaximal activity), the control logic in the device would then be able to automatically apply a Response Factor that would align the patient ventilatory reserve to their normal heart rate reserve.

The present invention is explained in greater detail in the following non-limiting Examples.

EXAMPLE 1

Tidal Volume as a Predictor of Minute Ventilation at Anaerobic Threshold and Peak Exercise: Automatic Calculation of Heart Rate Reserve for Adaptive Rate Pacing Although highly physiologic, minute ventilation (MV) sensors require empiric programming. If a pacemaker can automatically determine when a patient is at anaerobic threshold (AT) and peak exercise, the appropriate heart rate (HR) can be calculated at any level of metabolic demand. This study examined measurements from the ventilation pattern at low levels of exercise that predict AT and peak exercise.

Methods:

Twenty two patients with implanted pacemakers performed submaximal treadmill and maximal exercise to measure 1) Minute ventilation at the anaerobic threshold (ATMV) 2) Minute ventilation at peak exercise (PMV), and 3) Tidal volume at submaximal steady state exercise (ssVt).

Heart rates (HR) of 10 patients demonstrating intrinsic sinus node function corresponding to the observed minute ventilation at anaerobic threshold (ATMV) and minute ventilation at peak exercise (PMV) were compared to the predicted minute ventilation at anaerobic threshold (ATMVp) and predicted minute ventilation at peak exercise (PMVp) heart rates.

Predictability of heart rates at the anaerobic threshold and peak exercise, minute ventilation at anaerobic threshold (ATMV) and at peak exercise (PMV), was performed using a linear regression based on measurements of tidal volume at submaximal steady state exercise (ssVt).

Figure 4:
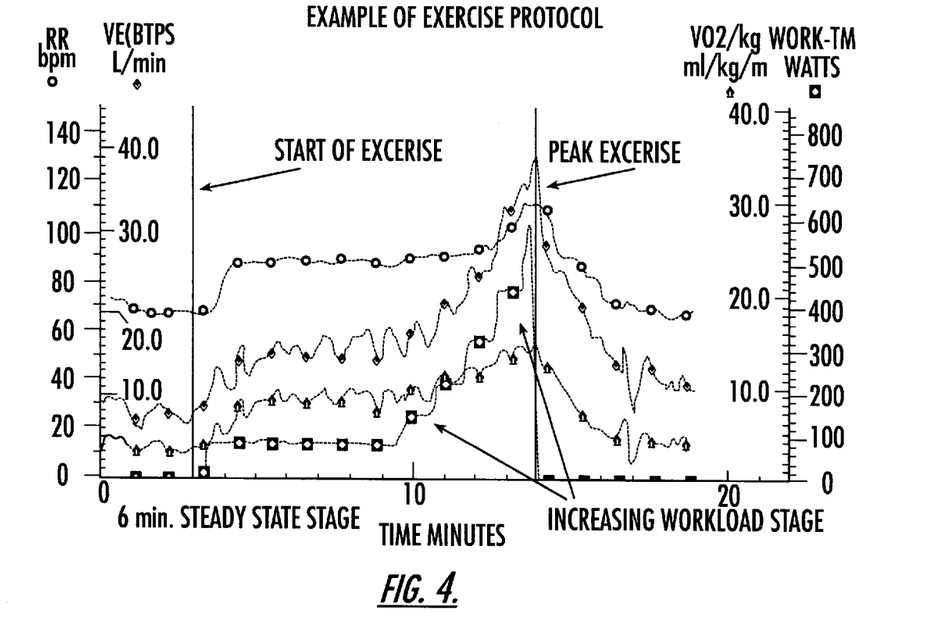

Exercise Protocol:

The protocol used in the study consisted of submaximal steady state exercise for a duration of six minutes progressing to peak exercise via two minute stages incrementally increasing the exercise workload. An example is given as FIG. 4.

Steady state tidal volume (Vt).

Figure 5:
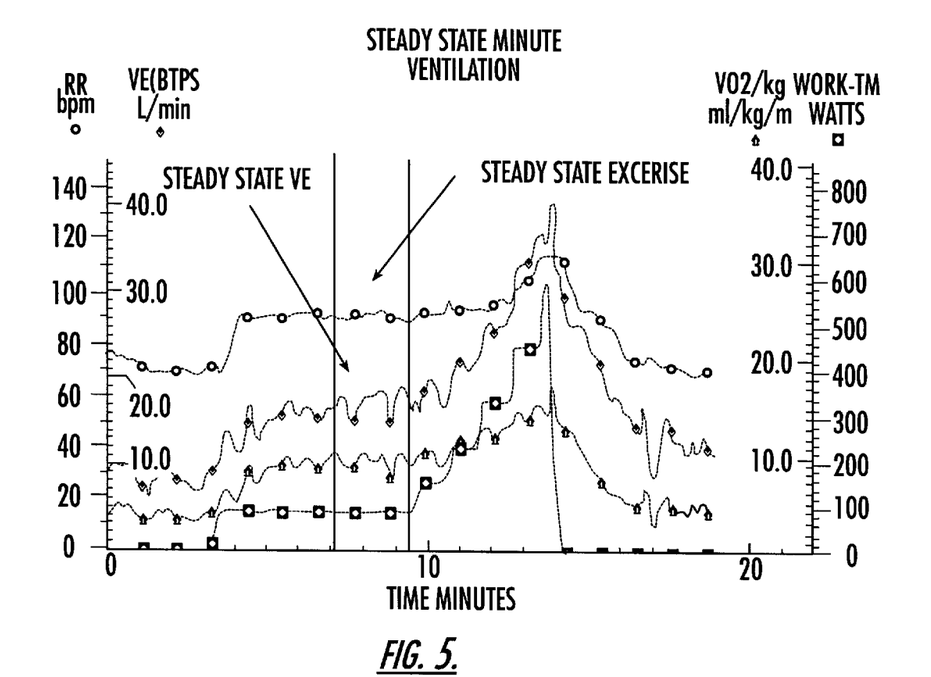
FIG. 5 is a metabolic analyzer measurement as in FIG. 4, illustrating steady state minute ventilation for a patient.
Figure 6:
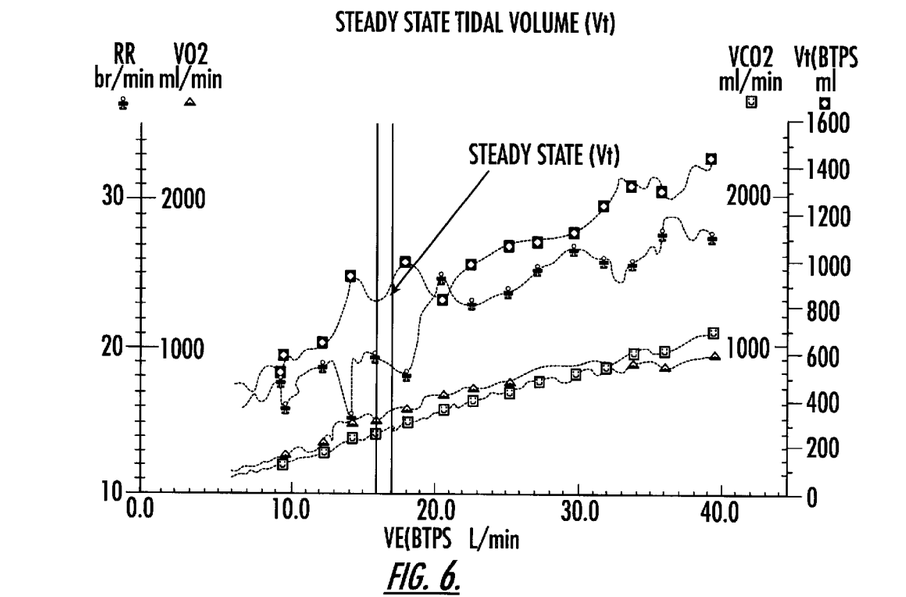
FIG. 6 is a metabolic analyzer measurement from a patient as in FIG. 4, illustrating steady state tidal volume.

The measure of steady state tidal volume (Vt) was performed once steady state exercise was determined. Steady state exercise was confirmed when oxygen uptake was consistent over the six minute steady state exercise period of the testing protocol. Steady state minute ventilation is illustrated in FIG. 5, and steady state tidal volume (Vt) is shown in FIG. 6.

Anaerobic Threshold MV.

The measure of anaerobic threshold minute ventilation (ATMV) was determined as the time in point that the carbon dioxide exceeded the oxygen uptake during incremental increase in exercise workload.

Figure 7:
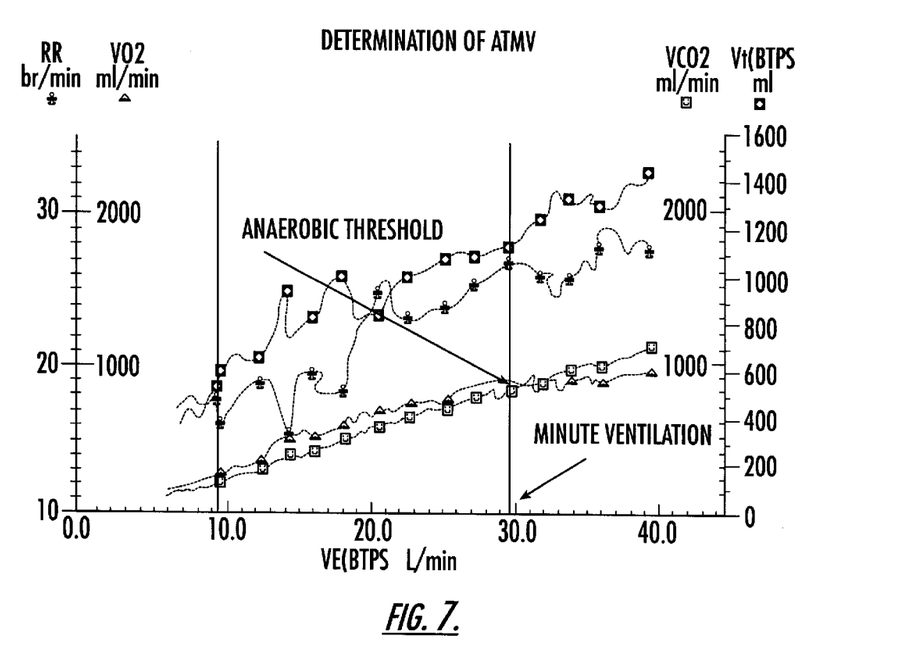
FIG. 7 is a metabolic analyzer measurement from a patient as in FIG. 4, illustrating the anaerobic theshold minute ventilation.
Figure 8:
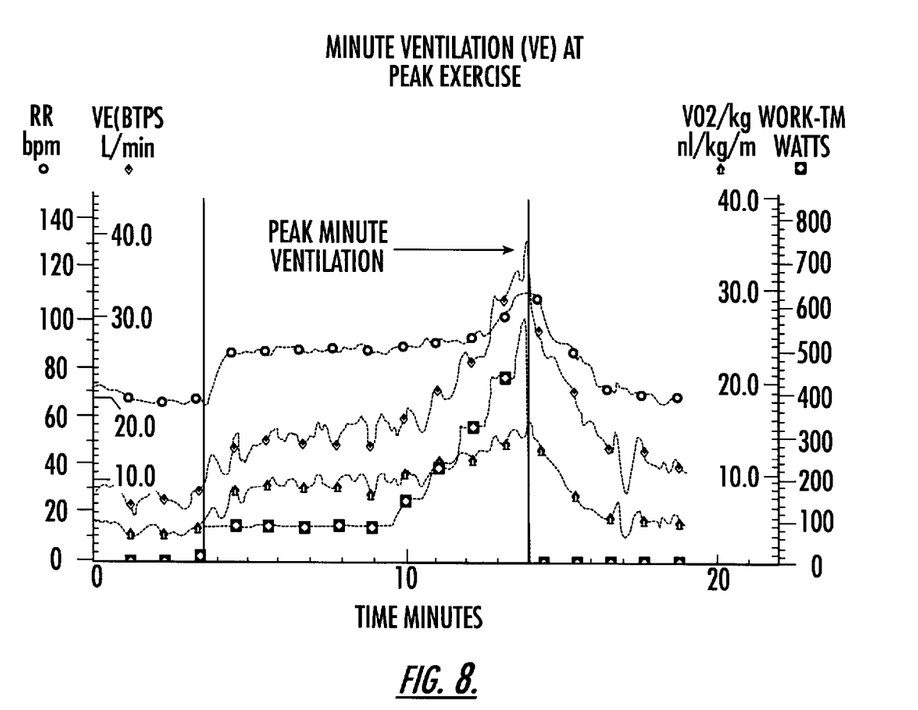
FIG. 8 is a metabolic analyzer measurement from a patient as in FIG. 4, illustrating minute ventilation at peak exercise.

The measure of anaerobic threshold minute ventilation (ATMV) was determined as the time in point that the carbon dioxide exceeded the oxygen uptake during incremental increase in exercise workload. An example of the determination of ATMV is given in FIG. 7, and an example of minute ventilation (VE) at peak exercise is given as FIG. 8.

Data analysis.

Predictability of ATMV, PMV and HR via ssVt was analyzed using a linear regression program available from SASS Institute, Cary, North Carolina USA, in accordance with known techniques.

Results.

The predicted minute ventilation at peak exercise (PMVp) is 73.0±20.6 liters per minute. The minute ventilation at the anaerobic threshold (ATMVp) is 46.1±13.0 liters per minute.

Figure 9:
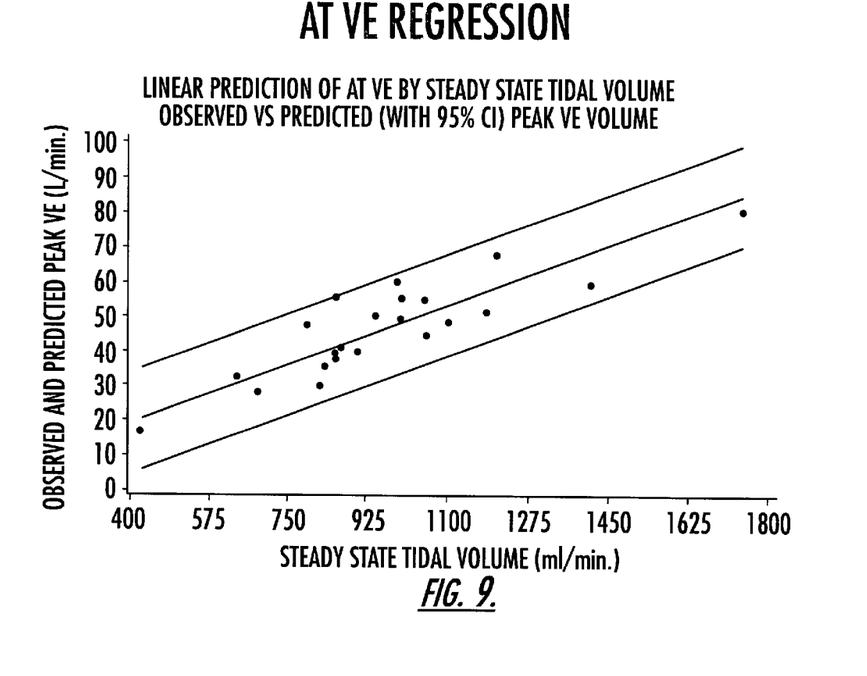
FIG. 9 is a linear prediction of anaerobic threshold VE (plotted as lines) compared with the observed anaerobic threshold VE (plotted as individual points) plotted against the steady state tidal volume in group of patients implanted with pacemakers.
Figure 10:
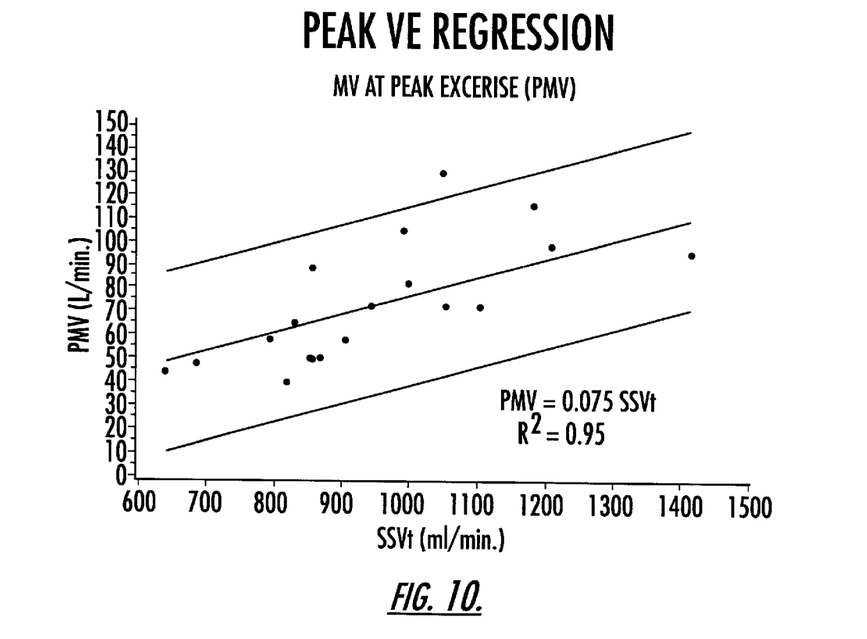
FIG. 10 is a linear prediction of peak minute ventilation (plotted as lines) compared with the observed peak exercise minute ventilation (plotted as individual points) in a group of patients implanted with pacemakers.

Difference in heart rates predicted, via submaximal steady state tidal volume estimates, at the anaerobic threshold (ATMVp) and peak exercise minute ventilation (PMVp) compared to the actual observed heart rates at anaerobic threshold (ATMV) and peak exercise minute ventilation (PMV) (See FIG. 9 and FIG. 10, rexpectively) Heart rate differences in the 10 patients are 7.4±4.6 ppm and 8.0±9.9 ppm respectively.

Conclusion.

Submaximal exercise steady state tidal volume measurements accurately predicts the anaerobic threshold minute ventilation (ATMV) and peak exercise minute ventilation (PMV). This allows the automatic calculation of metabolic reserve and heart rate at any intermediate exercise workload via the alignment of peak heart rate to peak exercise minute ventilation, without performing a maximal exercise test.

In the drawings and specification, there have been disclosed typical preferred embodiments of the invention and, although specific terms are employed, they are used in generic and descriptive sense only and not for the purposes of limitation, the scope of the invention being set forth in the following claims.

That which is claimed is:

1. A method for automatically determining the ventilatory threshold breakpoint for adaptive rate pacing without the need for directly measuring anaerobic threshold or ventilatory threshold in a human patient carrying an implanted pacemaker, said method comprising:

positioning a first sensing electrode in the heart or superior vena cava of said patient, said first sensing electrode connected to said implanted pacemaker;

positioning a second sensing electrode in the thoracic region of said patient and spaced apart from said first sensing electrode;

determining the chest wall impedance of said patient between said first sensing electrode and said second sensing electrode; then measuring the ventilation of said subject from said chest wall impedance during submaximal exercise by said patient; and then determining the ventilatory threshold breakpoint of said patient from said measured ventilation;

wherein said determining step is carried out by calculating a parameter from said measured ventilation, said parameter selected from the group consisting of respiratory rate change during submaximal exercise, tidal volume change during submaximal exercise, and tidal volume during steady state submaximal exercise, and then determining said ventilatory threshold breakpoint from said calculated parameter.

2. A method according to claim 1, wherein said second sensing electrode is positioned outside the pleural cavity of said patient.

3. A method according to claim 1, wherein said second sensing electrode is positioned on the surface of said implanted pacemaker.

4. A method according to claim 1, wherein said step of measuring the ventilation of said subject is carried out by measuring the minute ventilation (VE) of said subject.

5. A method according to claim 1, further comprising the step of:
measuring respiratory rate (RR) concurrently with said step of measuring the ventilation of said subject;
and wherein said determining step comprises determining the ventilatory threshold breakpoint of said patient from both said measured ventilation during submaximal exercise and said measured respiratory rate during submaximal exercise.

6. A method according to claim 5, further comprising the steps of:
determining the onset slope of tidal volume ($V_t$) during said submaximal exercise;
determining the onset slope of respiratory rate (RR) during said submaximal exercise;
determining the steady state of $V_t$ during said submaximal exercise;
determining the steady state of RR during said submaximal exercise;
determining minute ventilation (VE) during a rest period prior to or following said submaximal exercise;
and wherein said determining step comprises determining the ventilatory threshold breakpoint of said patient from all of said measured ventilation during submaximal exercise; said measured respiratory rate; the onset slope of tidal volume during said submaximal exercise; the onset slope of respiratory rate, the steady state of $V_t$ during submaximal exercise; and the steady state of RR during said submaximal exercise; VE during said submaximal exercise; and VE during said rest period.

7. A method according to claim 1, wherein said measuring step is initiated by operator control.

8. A method according to claim 1, wherein said step of determining the ventilatory threshold breakpoint is followed by the step of programming said pacemaker to reduce the rate of increase of the pacing rate at said determined ventilatory threshold.

9. A method according to claim 1, further comprising the step of determining the peak ventilation of said patient from said measured ventilation.

10. A method according to claim 9, further comprising the step of programming said pacemaker to match the maximum pacing rate of said pacemaker to said peak ventilation.

11. A method according to claim 10, wherein said programming step is carried out automatically without operator intervention.

12. A method for automatically matching the pacing rate of an adaptive rate pacemaker to the ventilatory threshold breakpoint and peak ventilation in a human subject carrying an implanted adaptive rate pacemaker without the need for a maximum exercise test on said subject, said method comprising:

positioning a first sensing electrode in the heart or superior vena cava of said patient, said first sensing electrode connected to said implanted pacemaker;

positioning a second sensing electrode in the thoracic region of said patient and spaced apart from said first sensing electrode;

determining the chest wall impedance of said patient between said first sensing electrode and said second sensing electrode;

measuring the ventilation of said subject from said chest wall impedance during submaximal exercise by said patient; and then calculating at least one parameter from said measured ventilation, said at least one parameter selected from the group consisting of respiratory rate change during submaximal exercise, tidal volume change during submaximal exercise, and tidal volume during steady state submaximal exercise; and then determining said ventilatory threshold breakpoint and said peak ventilation from said at least one calculated parameter; then programming said pacemaker to reduce the rate of increase of the pacing rate at said determined ventilatory threshold; and programming said pacemaker to match the maximum pacing rate of said pacemaker to said peak ventilation.

13. A method according to claim 12, wherein said second sensing electrode is positioned outside the pleural cavity of said patient.

14. A method according to claim 12, wherein said second sensing electrode is positioned on the surface of said implanted pacemaker.

15. A method according to claim 12, wherein said measuring step is initiated by operator control.

16. A method according to claim 12, wherein said programming steps are carried out automatically without operator intervention.

17. A rate-responsive cardiac pacemaker, comprising:
pacing means for pacing a patient's heart as a function of a pacing signal at a pacing rate up to a maximum pacing rate;
sensing means for sensing ventilation by said patient; and
control means operatively associated to said sensing means for determining a ventilatory threshold break point from said sensed ventilation;
said control means further determining a peak ventilation in response to said sensed ventilation.

18. A pacemaker according to claim 17, said sensing means comprising a chest wall impedance sensor.

19. A pacemaker according to claim 17;
said control means including means for modifying said pacing rate in response to said ventilatory threshold break point.

20. A pacemaker according to claim 17, said control means including means for matching said sensed ventilation to said maximum pacing rate.

21. A pacemaker according to claim 17, wherein said sensed ventilation is submaximal exercise sensed ventilation.

* * * * *

UNITED STATES PATENT AND TRADEMARK OFFICE
CERTIFICATE OF CORRECTION

PATENT NO. : 6,411,850 B1
DATED : June 25, 2002
INVENTOR(S) : Kay et al.

It is certified that error appears in the above-identified patent and that said Letters Patent is hereby corrected as shown below:

<u>Title page,</u>
Item [75], Inventors,
The information pertaining to Inventor "Heemells" should be deleted and replaced with the following:
-- Jan Pieter Heemels, Giessen, Germany --

Signed and Sealed this

Fifth Day of November, 2002

*Attest:*

*Attesting Officer*

JAMES E. ROGAN
*Director of the United States Patent and Trademark Office*